US008211853B2

(12) United States Patent
Chada et al.

(10) Patent No.: US 8,211,853 B2
(45) Date of Patent: Jul. 3, 2012

(54) METHOD OF PROMOTING APOPTOSIS OF DIFFERENTIATED ADIPOCYTES AND INCREASING ENDOGENOUS EXPRESSION OF SFRP-5 PEPTIDE BY ADMINISTRATION OF SFRP-5 PEPTIDE

(75) Inventors: Kiran K. Chada, New York, NY (US);
Roland Chouinard, Piscataway, NJ (US); Hena Ashar, Edison, NY (US);
Md. Abu Sayed, Cincinnati, OH (US)

(73) Assignee: HMGene Inc., Piscataway, NJ (US)

( * ) Notice: Subject to any disclaimer, the term of this patent is extended or adjusted under 35 U.S.C. 154(b) by 0 days.

(21) Appl. No.: 12/803,963

(22) Filed: Jul. 9, 2010

(65) Prior Publication Data

US 2011/0046045 A1 Feb. 24, 2011

(51) Int. Cl.
*A61K 38/00* (2006.01)
*A61P 3/06* (2006.01)
(52) U.S. Cl. .......................................... 514/1.1; 514/7.4
(58) Field of Classification Search ........................ None
See application file for complete search history.

(56) References Cited

U.S. PATENT DOCUMENTS

| 7,045,596 | B2 | 5/2006 | Umansky et al. |
| 7,879,544 | B2 | 2/2011 | Chada et al. |
| 2002/0155472 | A1 | 10/2002 | Czech et al. |
| 2003/0143610 | A1 | 7/2003 | Xu |
| 2004/0259789 | A1 | 12/2004 | Chada et al. |

FOREIGN PATENT DOCUMENTS

WO    WO 00/61631    10/2000

OTHER PUBLICATIONS

Melkonyan et al., PNAS, 94: 13636-13641, 1997.*
Anand et al. (2000) "In Vivo modulation of Hgmic reduces obesity", Nature Genetics, 24:377-380.
Flier, et al. (Apr. 1997) "Leptin Expression and action: New experimental paradigms", PNAS, 94:4242-4245.
Hu et al. (1998) "Tissue restricted expression of two human Frzbs in preadipocytes and pancreas", Bioch. Biophys. Res. Comm., 247:287-293.
Jaubert, et al. (1999) "Three new allelic mouse mutations that cause skeletal overgrowth involve the natriuretic peptide receptor C gene (Npr3)", PNAS, 96:10278-10283.
Jequier and Tappy (1999) "Regulation of Body Weight in Humans", Physiological Rev., 79:451-480.
Matsukawa, et al. (1999) "The natriuretic peptide clearance receptor locally modulates the physiological effects of the natriuretic peptide system", PNAS, 96:7403-7408.
Samad, et al. (Jun. 1998) "Tissue factor gene expression in the adipose tissues of obese mice", PNAS, 95:7591-7596.
Soukas et al. (2000) "Leptin-specific patterns of gene expression in white adipose tissue", Genes and Development, 14:963-980.
Requirement for Restriction/Election issued Dec. 29, 2005 in connection with U.S. Appl. No. 10/768,566.
Response to Dec. 29, 2005 Requirement for Restriction filed Jan. 30, 2006 in connection with U.S. Appl. No. 10/768,566.
Non-final Office Action issued Apr. 19, 2006 in connection with U.S. Appl. No. 10/768,566.
Amendment in Response to Apr. 19, 2006 Office Action and Petition for a Three-month Extension of Time filed Oct. 26, 2006 in connection with U.S. Appl. No. 10/768,566.
Final Office Action issued Jan. 10, 2007 in connection with U.S. Appl. No. 10/768,566.
Amendment in Response to Jan. 10, 2007 Final Office Action filed Jan. 29, 2007 in connection with U.S. Appl. No. 10/768,566.
Interview Summary issued Feb. 9, 2007 in connection with U.S. Appl. No. 10/768,566.
Advisory Action Before the Filing of an Appeal Brief issued Mar. 5, 2007 in connection with U.S. Appl. No. 10/768,566.
Response to Mar. 5, 2007 Advisory Action and Supplemental Response to Jan. 10, 2007 Final Office Action filed Mar. 9, 2007 in connection with U.S. Appl. No. 10/768,566.
Advisory Action Before the Filing of an Appeal Brief issued Apr. 16, 2007 in connection with U.S. Appl. No. 10/768,566.
Pre-appeal Brief Request for Review and Notice of Appeal from the Examiner's Decision to the Board of Patent Appeals and Interferences, May 10, 2007 with U.S. Appl. No. 10/768,566.
Communication in Response to Nov. 8, 2007 Notification of Non-compliant Appeal Brief and amended Appeal Brief filed Dec. 13, 2007 with U.S. Appl. No. 10/768,566.
Examiner's Answer issued Mar. 11, 2008 in connection with U.S. Appl. No. 10/768,566.
Reply Brief to Examiner's Mar. 11, 2008 Answer filed May 15, 2008 in connection with U.S. Appl. No. 10/768,566.
Communication in Response to Jan. 21, 2009 Notification of Non-compliant Appeal Brief and amended Appeal Brief filed Feb. 9, 2009 in connection with U.S. Appl. No. 10/768,566.
Board of Patent Appeals and Interferences Decision—Examiner Affirmed issued May 12, 2010 in connection with U.S. Appl. No. 10/768,566.

* cited by examiner

*Primary Examiner* — Gyan Chandra
(74) *Attorney, Agent, or Firm* — Gary J. Gershik; Cooper & Dunham LLP

(57) ABSTRACT

Disclosed is a method of reducing the amount of adipose tissue in a subject comprising administering to the subject an amount of an sFRP-5 peptide effective to reduce the amount of adipose tissue, or an amount of a molecule effective to stimulate expression of the sFRP-5 peptide in the subject. Also disclosed is a screen for molecules that can reduce the amount of adipose tissue in a subject.

6 Claims, 7 Drawing Sheets

METHOD OF PROMOTING APOPTOSIS OF DIFFERENTIATED ADIPOCYTES AND INCREASING ENDOGENOUS EXPRESSION OF SFRP-5 PEPTIDE BY ADMINISTRATION OF SFRP-5 PEPTIDE

This application claims benefit of U.S. Ser. No. 10/630,423, filed Jul. 29, 2003, which claims benefit of U.S. Provisional Application No. 60/398,785, filed Jul. 29, 2002, and U.S. Provisional Application No. 60/478,206, filed Jun. 12, 2003, the contents of all of which are hereby incorporated by reference.

Throughout this document various publications or patents are referenced to describe the state of the art to which the invention pertains. Each of the referenced publications and patents is incorporated by reference herein.

FIELD OF THE INVENTION

The present invention relates to the field of molecular biology, human metabolism and physiology. In particular, this invention provides for an sFRP-5 polypeptide and methods of administration of such an sFRP-5 polypeptide to a subject for the treatment of obesity and other metabolic disorders related to an overabundance of adipose tissue.

BACKGROUND OF THE INVENTION

Obesity, or an excess of body fat relative to lean body mass, is a serious health problem in the United States and abroad. A person is clinically obese if he or she has excess adipose tissue. More particularly, for purposes of the present invention, a person is obese if the person's body mass index equals or exceeds 27 kg/m2 and the person has excess adipose tissue.

Statistics suggest that more than 25% of the United States population and 27% of the Canadian population are overweight. Complications of obesity include, among others, diabetes mellitus, hypertension, hyperlipoproteinemia, cardiac diseases (atherosclerotic disease, congestive heart failure, etc.), pulmonary diseases (e.g., sleep apnea, restrictive lung disease), cerebrovascular injury, cancers (including breast, uterine, colon, and prostate), gall bladder disease (stones, infection), toxemia during pregnancy, risks during surgery (e.g., pneumonia, wound infection, thrombo-phlebitis), gout, decreased fertility, degenerative arthritis, and early mortality. Psychological complications of obesity include poor self-image and poor body-image. Social complications of obesity include discrimination in jobs, education and marriage. Despite the known associated risks, a significant portion of the population is unable to lose weight or maintain weight loss. Obesity is now considered the second leading cause of preventable death in the United States, second only to smoking, with an estimated 300,000 deaths annually. Accordingly, reduction of the prevalence of obesity in the adult population to less than 20% is included by the US Department of Health and Human Services among the national health objectives.

The human tragedy notwithstanding, the monetary costs of obesity are staggering. The total cost attributable to obesity in 1995 has been estimated to be in excess of $99 billion, with approximately $51.64 billion paid in direct medical costs. Overall, the direct costs associated with obesity represent 5.7% of the annual United States national health expenditure. Thus, it is clear that the magnitude of this problem produces a significant demand for safe and effective treatments for obesity. Obesity has a number of known and suspected etiologies. See A. Sclafani, "Animal Models of Obesity: Classification and Characterization," Int. J. Obesity 8, 491-508 (1984); G. A. Bray, "Classification and Evaluation of the Obesities," Med. Clin. N. Am. 73, 161-184 (1989). While it is generally known that overeating and inactivity are factors that lead to obesity, there is substantial evidence of genetic contribution to obesity. Although the molecular characterization of genetic pathways associated with obesity is incomplete, several recent advances into the elucidation of these pathways have been made. Research indicates that there are several genes that act independently or in combination to modulate metabolic pathways associated with excess adipose tissue accumulation. The presence of these various pathways suggests a complex system of obesity regulation, a system that has not yet been fully defined.

Some mouse models for obesity include obese (ob/ob), agouti (Ay/a), tubby (tub), fat (fa/fa) and diabetes (db/db). These models have proven to be effective in the molecular characterization of these genetic loci because of their ability to simplify the heritability of complex traits.

One gene responsible for the autosomal recessive mouse obesity mutation tub has been identified by positional cloning and shown to be associated with maturity-onset obesity (U.S. Pat. No. 5,776,762). Identification of the tub gene and the protein it encodes may lead to the development of agents that will function to modulate either the protein or gene expression. However, a disadvantage of this system is the ubiquitous nature of the gene, in that the gene is expressed in high levels in the brain, eye and testis, and at lower levels in various adult and fetal tissues, including small and large intestine, ovary and adipose tissue. Although the gene may be used as a probe for identification of other tubby polypeptides, development of agents to modulate the expression of these polypeptides would not be specific to a particular tissue.

Similarly, the ob gene has recently been cloned. The ob gene encodes a protein known as leptin, which has been implicated in an energy feedback loop responsible for controlling vertebrate energy balance. Serum levels of leptin are increased proportionately to excess adipose accumulation as a result of increased expression in hypertrophic fat cells in obese patients. In vitro studies have indicated that insulin and glucocorticoids upregulate leptin mRNA expression in a synergistic manner. The subsequent expression of the protein product thereby functions to stimulate metabolic activity. The promoter of the ob gene has been cloned and is a candidate for pharmacological control (U.S. Pat. No. 6,124,448).

In addition to cloning the promoter of the ob gene, attempts at obesity regulation have also been made through modulation of the ob gene. The ob/ob mouse is a model of obesity and diabetes that carries an autosomal recessive trait linked to a mutation in the sixth chromosome (Yiying Zhang et al. Nature 372: 425-32 (1994). Pharmacological agents have therefore been developed to mimic the action of the ob gene encoded protein and assist in regulation of appetite and metabolism. However, the majority of obese humans actually have normal or somewhat elevated levels of leptin as compared to lean humans leading some to hypothesize that human obesity may be more related to leptin resistance rather than leptin deficiency. Recent clinical trials have shown that leptin may be useful for a certain subset of patients, but not for the treatment of obesity generally (Gura, T., Science 1999, 286 (5441): 881-2).

Using molecular and classical genetic markers, the ob and db genes have been mapped to proximal chromosome 6 and midchromosome 4, respectively (Bahary et al., Proc. Nat. Acad. Sci. USA, 87:8642-8646 (1990); Friedman et al., Genomics, 11:1054-1062 (1991)). In both cases, the mutations map to regions of the mouse genome that are syntenic with human, which suggested that if there were human homologs of ob and db, they would likely map, respectively, to human chromosomes 7q and 1p. In fact, the human homologs have been positionally cloned-OB (the human homolog for ob) has been cloned to human chromosome 7q31.3 (Isse, et al. J Biol Chem 1995 Nov. 17; 270 (46): 27728-33). LEPR (the human homolog for db) has been mapped to human chromosome 1p31 (Thompson, et al. Genomics 1997; 39(2):227-30). Defects in the leptin receptor gene results in obesity in other mammalian species: the fa gene in the rat encodes the leptin receptor.

Traditionally, pharmacological approaches to weight loss or prevention of weight gain have relied either on reduction of food intake or on reduction of nutrient absorption. Drugs of the first group, which include Redux (American Home Products) and Meridia (Knoll Pharmaceuticals), affect neurotransmitter activity in the brain, resulting in appetite suppression and decreased food intake. While effective in producing a moderate weight loss in some proportion of patients these medications are associated with a number of adverse side effects.

Drugs of the second group, including Xenical (Hoffmann-La Roche), reduce total absorption of fat from the gastrointestinal tract. However, inhibition of fat absorption by this drug can lead to avitaminosis since successful uptake of fat soluble vitamins from the intestines is impaired in the absence of fat. Additionally, these drugs produce unpleasant side-effects, such as steatorrhea, which reduce patient compliance. Other health problems have been shown to stem directly or indirectly from use of the drug as well such as an increased incidence of breast cancer.

Consequently, focus has since shifted away from these group one and two pharmaceuticals and instead towards targeting genes and gene products which function at the level of the adipose tissue itself. SFRP-5 is such a protein which we have shown is modulated in obesity, regulates its own expression in an autocrine fashion and results in significant weight loss when overexpressed in mice.

SUMMARY OF THE INVENTION

This invention provides a method for treating an obese subject or a subject having complications related to obesity including but not limited to diabetes mellitus, hypertension, hyperlipoproteinemia, cardiac diseases (atherosclerotic disease, congestive heart failure, etc.), pulmonary diseases (e.g., sleep apnea, restrictive lung disease), cerebrovascular injury, cancers (including breast, uterine, colon, and prostate), gall bladder disease (stones, infection), toxemia during pregnancy, risks during surgery (e.g., pneumonia, wound infection, thrombo-phlebitis), gout, decreased fertility, degenerative arthritis, and early mortality by administering to said subject a therapeutically effective amount of an sFRP-5 polypeptide or an active fragment thereof.

DETAILED DESCRIPTION OF THE INVENTION

Figure 1:
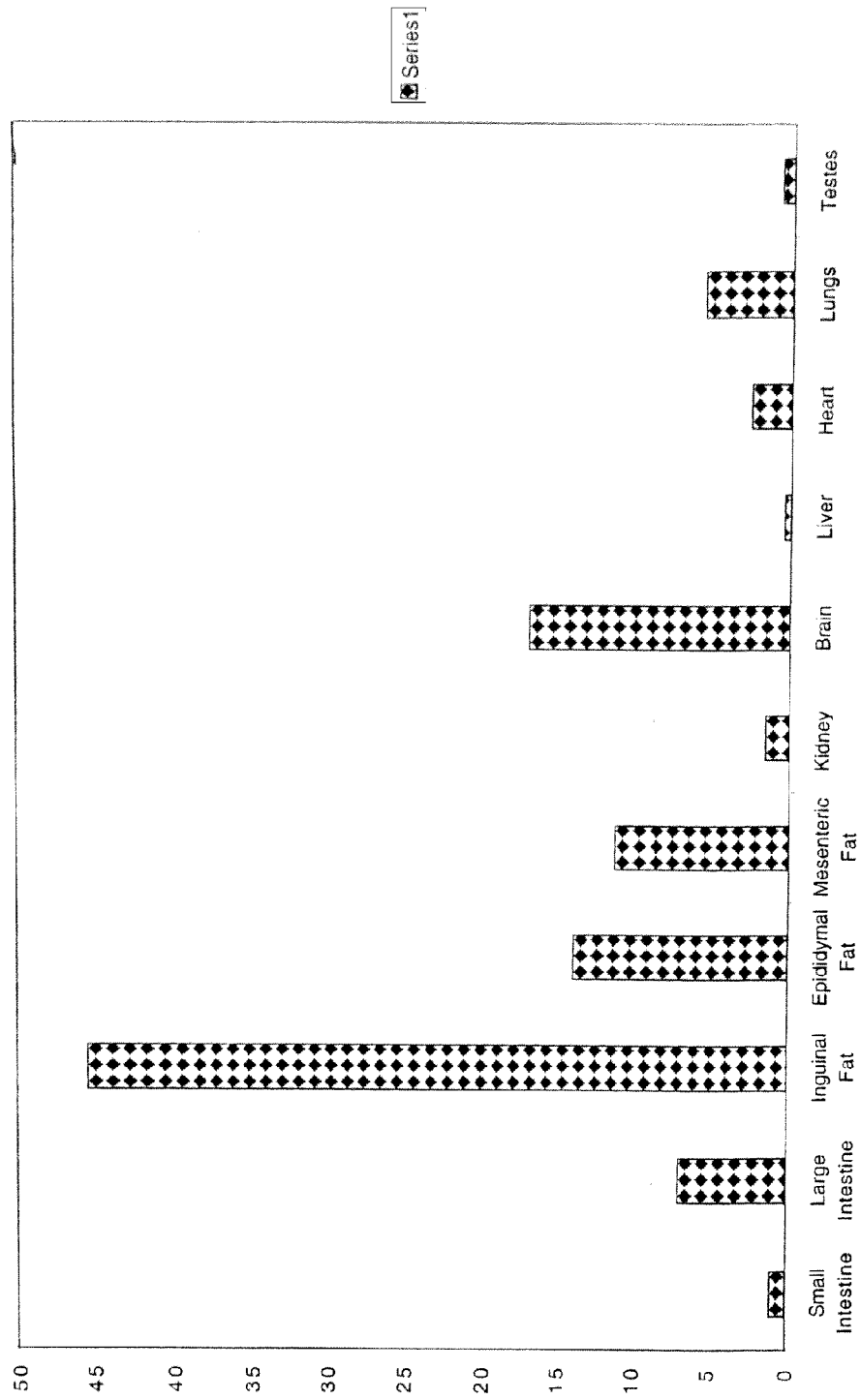
FIG. 1 represents the tissue distribution of sFRP-5 expression in wild-type mice.

This invention provides for a method of treating a subject in need of a treatment for an excess of adipose tissue, overweight, obesity and other obesity related complications including but not limited to diabetes mellitus, hypertension, hyperlipoproteinemia, cardiac diseases (atherosclerotic disease, congestive heart failure, etc.), pulmonary diseases (e.g., sleep apnea, restrictive lung disease), cerebrovascular injury, cancers (including breast, uterine, colon, and prostate), gall bladder disease (stones, infection), toxemia during pregnancy, risks during surgery (e.g., pneumonia, wound infection, thrombo-phlebitis), gout, decreased fertility, degenerative arthritis, and early mortality comprising the administration of a therapeutic amount of an sFRP-5 polypeptide or an active fragment thereof parenterally as described herein.

Polypeptides

The polypeptide of the subject invention comprises an amino acid sequence which has at least 90% identity, more preferably at least 91% identity, yet more preferably at least 92% identity, yet more preferably at least 95% identity, most preferably at least 96-99% identity, to that of the entire length of SEQ ID NO. 1.

The sFRP-5 polypeptides of the invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the polypeptides are also included in the invention. A fragment is a polypeptide having an amino acid sequence that entirely is the same as part, but not all, of the amino acid sequence of the polypeptides. Preferred fragments include, for example, truncation polypeptides having the amino acid sequence of the polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding regions, and high antigenic index regions. Other preferred fragments are biologically active fragments. Biologically active fragments are those that mediate the peptides activity, including those with a similar activity or an improved activity, or with a decreased undesirable activity. Also included are those that are antigenic or immunogenic in an animal, especially in a human. Preferably, all of these polypeptide fragments retain the biological activity of the identified peptide, including any antigenic activity. Variants of the defined sequence and fragments also form part of the present invention. Preferred variants are those that vary from the referents by conservative amino acid substitutions.

The polypeptides of the invention can be prepared in any suitable manner. If produced in situ; the polypeptides may be purified from appropriate sources, e.g., cells from human or mouse.

Alternatively, the availability of nucleic acid molecules encoding the polypeptides enables production of the proteins using in vitro expression methods known in the art. For example, a cDNA or gene may be cloned into an appropriate in vitro transcription vector, for in vitro transcription, followed by cell-free translation in a suitable cell-free translation system. In vitro transcription and translation systems are commercially available, e.g., from Promega Biotech, Madison, Wis., or Invitrogen, Carlsbad, Calif. Rockville, Md. While in vitro transcription and translation is not the method of choice for preparing large quantities of the protein, it is ideal for preparing small amounts of native or mutant proteins for research purposes, particularly since it allows the incorporation of radioactive nucleotides.

According to a preferred embodiment, larger quantities of the encoded polypeptide may be produced by expression in a suitable prokaryotic or eukaryotic system. For example, part or all of a DNA molecule, such as the coding portion of an identified sequence may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA into the host cell. Such regulatory elements required for expression include promoter sequences, transcription initiation sequences and, optionally, enhancer sequences.

Secretion signals may be used to facilitate purification of the resulting protein. The coding sequence for the secretion peptide is operably linked to the 5' end of the coding sequence for the protein, and this hybrid nucleic acid molecule is inserted into a plasmid adapted to express the protein in the host cell of choice. Plasmids specifically designed to express and secrete foreign proteins are available from commercial sources. For example, if expression and secretion is desired in *E. coli*, commonly used plasmids include pTrcPPA (Pharmacia); pPROK-C and pKK233-2 (Clontech); and pNH8a, pNH16a, pcDNAII and pAX (Stratagene), among others.

The proteins produced by in vitro transcription and translation or by gene expression in a recombinant prokaryotic or eukaryotic system may be purified according to methods known in the art. Recombinant proteins can be purified by affinity separation, such as by immunological interaction with antibodies that bind specifically to the recombinant protein or fusion proteins such as His tags, as described below. Such methods are commonly used by skilled practitioners.

As mentioned, the proteins can be produced and fused to a "tag" protein in order to facilitate subsequent purification. These fusion proteins are produced by operably-linking the nucleic acid coding sequence of the "tag" protein to the coding sequence of the protein of interest, and expressing the fused protein by standard methods. Systems are commercially available that comprise a plasmid containing an expression cassette with the "tag" protein coding sequence and a polylinker into which a coding sequence of interest can be operably ligated. These fusion protein systems further provide chromatography matrices or beads which specifically bind the "tag" protein thereby facilitating the fusion protein purification. These fusion protein systems often have the recognition sequence of a protease at or near the junction of the "tag" protein and the protein of interest so that the "tag" protein can be removed if desired. Fusion protein systems include, but are not limited to, the His-6-tag system (Quiagen) and the glutathione-S-transferase system (Pharmacia).

The proteins of the invention, prepared by one of the aforementioned methods, may be analyzed according to standard procedures. For example, the protein may be subjected to amino acid composition, amino acid sequence, or protein concentration analysis according to known methods.

Using appropriate amino acid sequence information, synthetic proteins of the present invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

Polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography (HPLC) or fast protein liquid chromatography (FPLC) is employed for purification. Well known techniques for refolding proteins may be employed to regenerate active conformation when the polypeptide is denatured during isolation and or purification.

The invention provides a pharmaceutical composition comprising an sFRP-5 peptides encoded by SEQ ID NO: 2 and its parenteral administration to a subject in need of such a pharmaceutical composition for the condition of obesity and related conditions as defined below.

DEFINITIONS

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626-646 and Rattan et al., "Protein Synthesis: Posttranslational Modifications and Aging", Ann NY Acad Sci (1992) 663:48-62.

"Variant" as the term is used herein, is a polypeptide that differs from a reference polypeptide but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polypeptide may be naturally occurring such as an allelic variant, or it may be a variant that is not known to occur naturally. Non-naturally occurring variants of polypeptides may be made by mutagenesis techniques or by direct synthesis.

The term "substantially the same" refers to nucleic acid or amino acid sequences having sequence variation that do not materially affect the nature of the protein (i.e. the structure, stability characteristics, substrate specificity and/or biological activity of the protein). With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1286, J. Theor. Biol. 119:205).

"Identity" and "similarity" can be readily calculated by known methods. Amino acid sequences can be compared using computer programs that align the similar sequences of the amino acids thus define the differences. In preferred methodologies, the BLAST programs (NCBI) and parameters used therein are employed. However, equivalent alignments and similarity/identity assessments can be obtained through the use of any standard alignment software.

The term "substantially pure" refers to a preparation comprising at least 60% by weight the compound of interest (e.g., polypeptide). More preferably, the preparation comprises at least 75% by weight, and most preferably 90-99% by weight, the compound of interest. Purity is measured by methods appropriate to the compound of interest (e.g. chromatographic methods, polyacrylamide gel electrophoresis, HPLC analysis, and the like).

"Obesity" is defined as a body mass index (BMI) of 30 kg/m.sup.2 or more (National Institute of Health, Clinical Guidelines on the Identification, Evaluation, and Treatment of Overweight and Obesity in Adults (1998)). However, the invention is also intended to include adisease, disorder, or condition that is characterized by a body mass index (BMI) of 25 kg/m.sup.2 or more, 26 kg/m.sup.2 or more, 27 kg/m.sup.2 or more, 28 kg/m.sup.2 or more, 29 kg/m.sup.2 or more, 29.5 kg/m.sup.2 or more, or 29.9 kg/m.sup.2 or more, all of which are typically referred to as overweight (National Institute of Health, Clinical Guidelines on the Identification, Evaluation, and Treatment of Overweight and Obesity in Adults (1998)).

"Subject", as used herein, can refer to a mammal, e.g., a human, or to an experimental or naturally occurring animal disease model. The subject can also be a non-human animal, e.g., a horse, cow, goat, or other domestic animal. A subject, e.g., a human subject, can also be a patient, i.e., an individual receiving medical attention, care, or treatment.

Human sFRP-5 is *homo sapiens* secreted frizzled-related protein 5, having accession number NM 003015, and the amino acid sequence (SEQ ID NO: 1):

```
MRAAAAAGGVRTAALALLLGALHWAPARCEEYDYYGWQAEPLHGRSY

SKPPQCLDIPADLPLCHTVGYKRMRLPNLLEHESLAEVKQQASSWLP

LLAKRCHSDTQVFLCSLFAPVCLDRPIYPCRSLCEAVRAGCAPLMEA

YGFPWPEMLHCHKFPLDNDLCIAVQFGHLPATAPPVTKICAQCEMEH

SADGLMEQMCSSDFVVKMRIKEIKIENGDRKLIGAQKKKKLLKPGPL

KRKDTKRLVLHMKNGAGCPCPQLDSLAGSFLVMGRKVDGQLLLMAVY

RWDKKNKEMKFAVKFMFSYPCSLYYPFFYGAAEPH
``` and is encoded by nucleotide sequence (SEQ ID NO: 2):

```
  1 gaggcgccag gatcagtcgg ggcaccgca gcgcaggctg ccacccacct gggcgacctc 61 cgcggcggcg gcggcggcgg ctgggtagag tcagggccgg gggcgcacgc cggaacacct 121 gggccgccgg gcaccgagcg tcgggggggct gcgcggcgcg accctggaga gggcgcagcc
```

-continued

```
 181 gatgcgggcg gcggcggcgg cgggggcgt gcggacggcc gcgctggcgc tgctgctggg 241 ggcgctgcac tgggcgccgg cgcgctgcga ggagtacgac tactatggct ggcaggccga 301 gccgctgcac ggccgctcct actccaagcc gccgcagtgc cttgacatcc ctgccgacct 361 gccgctctgc cacacggtgg gctacaagcg catgcggctg cccaacctgc tggagcacga 421 gagcctggcc gaagtgaagc agcaggcgag cagctggctg ccgctgctgg ccaagcgctg 481 ccactcggat acgcaggtct tcctgtgctc gctctttgcg cccgtctgtc tcgaccggcc 541 catctacccg tgccgctcgc tgtgcgaggc cgtgcgcgcc ggctgcgcgc cgctcatgga 601 ggcctacggc ttcccctggc ctgagatgct gcactgccac aagttccccc tggacaacga 661 cctctgcatc gccgtgcagt tcgggcacct gcccgccacc gcgcctccag tgaccaagat 721 ctgcgcccag tgtgagatgg agcacagtgc tgacggcctc atggagcaga tgtgctccag 781 tgactttgtg gtcaaaatgc gcatcaagga gatcaagata gagaatgggg accggaagct 841 gattggagcc cagaaaaaga agaagctgct caagccgggc cccctgaagc gcaaggacac 901 caagcggctg gtgctgcaca tgaagaatgg cgcgggctgc ccctgcccac agctggacag 961 cctggcgggc agcttcctgg tcatgggccg caaagtggat ggacagctgc tgctcatggc 1021 cgtctaccgc tgggacaaga agaataagga gatgaagttt gcagtcaaat tcatgttctc 1081 ctaccctgc tccctctact acccttctt ctacggggcg gcagagcccc actgaagggc 1141 actcctcctt gccctgccag ctgtgccttg cttgccctct ggccccgccc caacttccag 1201 gctgacccgg ccctactgga gggtgttttc acgaatgttg ttactggcac aaggcctaag 1261 ggatgggcac ggagcccagg ctgtcctttt tgacccaggg gtcctggggt ccctgggatg 1321 ttgggcttcc tctctcagga gcagggcttc ttcatctggg tgaagacctc agggtctcag 1381 aaagtaggca ggggaggaga gggtaaggga aaggtggagg ggctcagggc accctgaggc 1441 ggaggtttca gagtagaagg tgatgtcagc tccagctccc ctctgtcggt ggtggggcct 1501 caccttgaag agggaagtct caatattagg ctaagctatt tgggaaagtt ctccccaccg 1561 cccctgtacg cgtcatccta gccccctta ggaaaggagt tagggtctca gtgcctccag 1621 ccacaccccc tgccttcccc agcttgccca tttccctgcc ccaaggccca gagctccccc 1681 cagactggag agcaagccca gcccagcctc ggcatagacc cccttctggt ccgcccgtgg 1741 ctcgattccc gggattcatt cctcagcctc tgcttctccc ttttatccca ataagttatt 1801 gctactgctg tgaggccata ggtactagac aaccaataca tgcagggttg ggttttctaa 1861 tttttttaac tttttaatta aatcaaaggt cgacgcgcgg ccgcg
```

SFRP-5 and Adipogenesis

The sFRP-5 gene is a member of the sFRP family, which regulate the Wnt signal transduction pathway. Wnts are a family of paracrine/autocrine factors which affect cell growth and proliferation. Wnt ligand binds to its cell surface receptor Frizzled. Frizzled then signals through Dishevelled to inhibit the kinase activity of a complex which contains glycogen synthase kinase 3 (GSK3), Axin, β-catenin and other proteins. When the complex is phosphorylated, β-catenin is targeted for rapid degradation. When the complex is hypophosphorylated due to Wnt signaling, β-catenin is stabilized and translocates to the nucleus where it binds the TCF/LEF family of transcription factors which in turn regulate the wnt target genes. The role of wnt signalling in adipocyte biology has been investigated, but has proven unpredicatble in that there are several species of wets, frizzleds, and sFRPs that interacct. For example, Ross, et al. (Science 289:950-953) have shown that wnt signaling through wnt 10b inhibits adipogenesis in the 3T3-F442A in vitro adipocyte model system. Therefore, if sFRP-5 were to inhibit the Wnt 10b pathway (which has not been shown experimentally) it would be expected that the effect of sFRP-5 would be promotion of adipogenesis. However, in experiments performed by the same group (Longo, et al. (J Biol. Chem., 2002, Oct. 11; 277(41):38239-44)) it was shown that wnt signalling through wnt 1 in the 3T3-L1 in vitro adipocyte model system protects the adipocytes from apoptosis. Thus, were sFRP-5 to inhibit wnt signalling through wnt 1, then the effect of sFRP-5 would be to promote apoptosis of adipocytes and reduce adiposity in the animal. In fact, others have hypothesized that sFRP-5 may play a role in adipogenesis, but have not been able to show a priori whether an increase of sFRP-5 activity or a decrease in sFRP-5 activity would result in a positive impact on adiposity and body weight (see U.S. Patent Application Publication No. 2003/0143610). The experiments performed by us and described below, including the nature of sFRP-5 autoregulation in cell culture and the effects of sFRP-5 overexpression in transgenic mice, illustrate that an increase in sFRP-5 activity would be beneficial in the reduction of adipocytes and the treatment of obesity.

Figure 2:
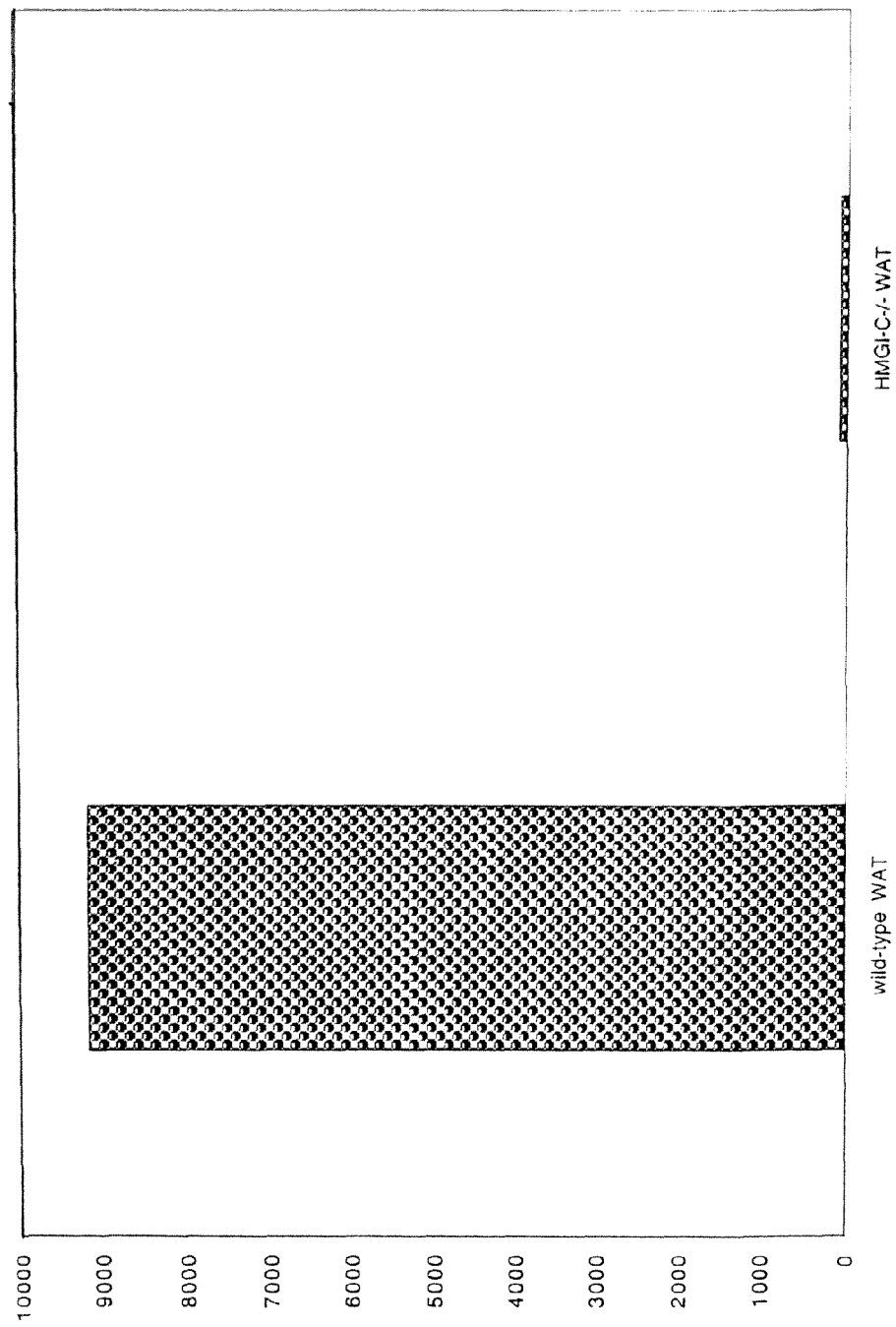
FIG. 2 represents the dependence of sFRP-5 expression on HMGI-C in the white adipose tissue (WAT) of wild-type mice versus HMGI-C−/− mice.
Figure 3:
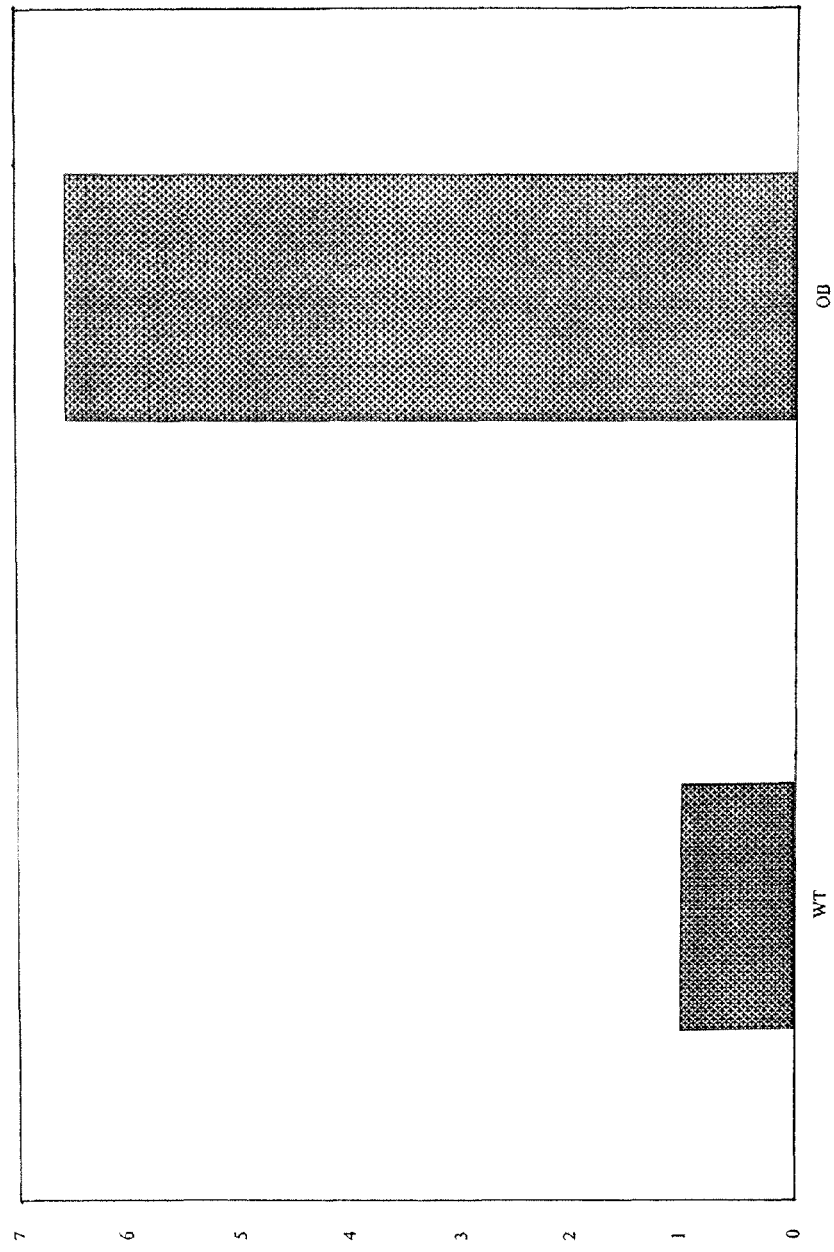
FIG. 3 represents the differential expression of sFRP-5 in the adipose of wild type versus obese mice.
Figure 4:
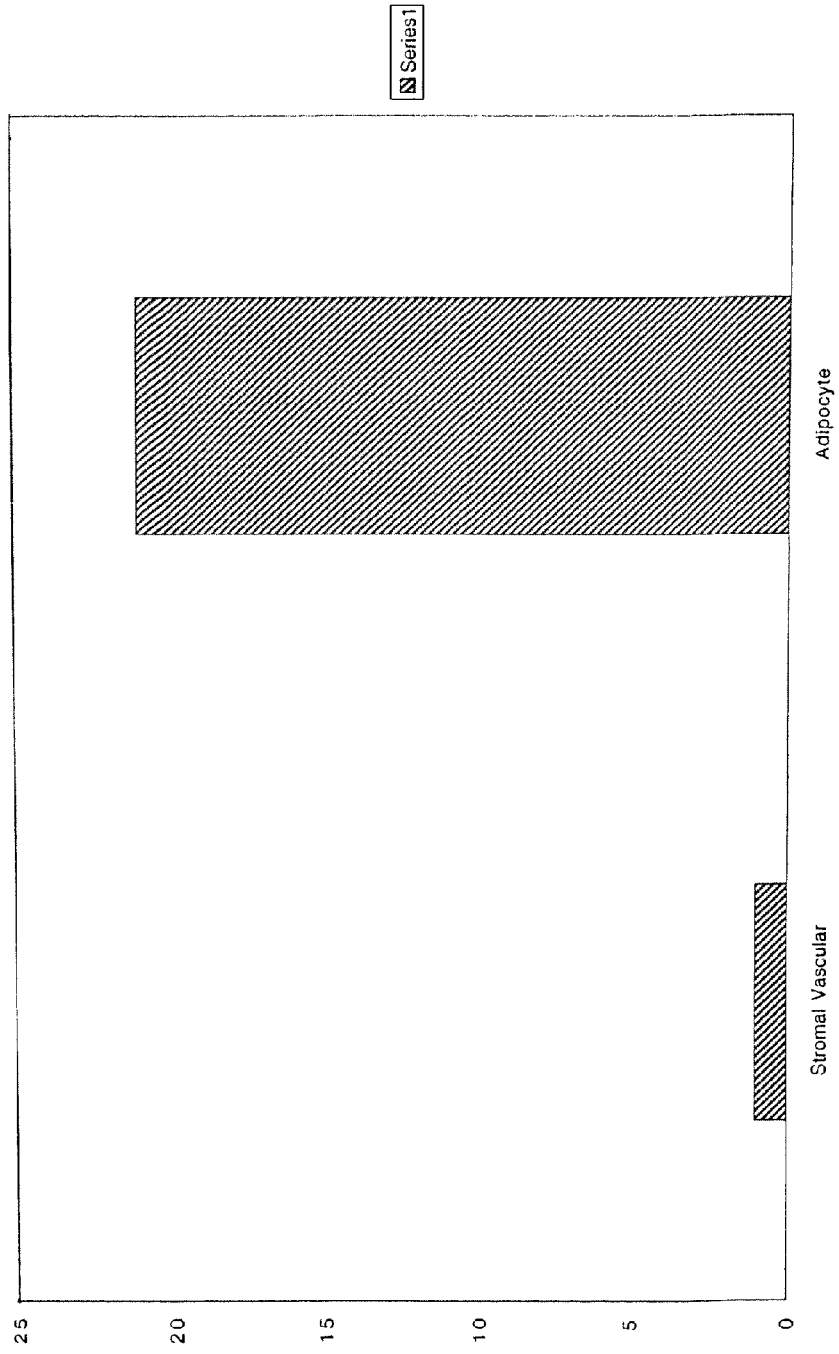
FIG. 4 represents the differential expression of sFRP-5 in cells of the stromal vascular fraction (preadipocytes) versus differentiated adipocytes.
Figure 5:
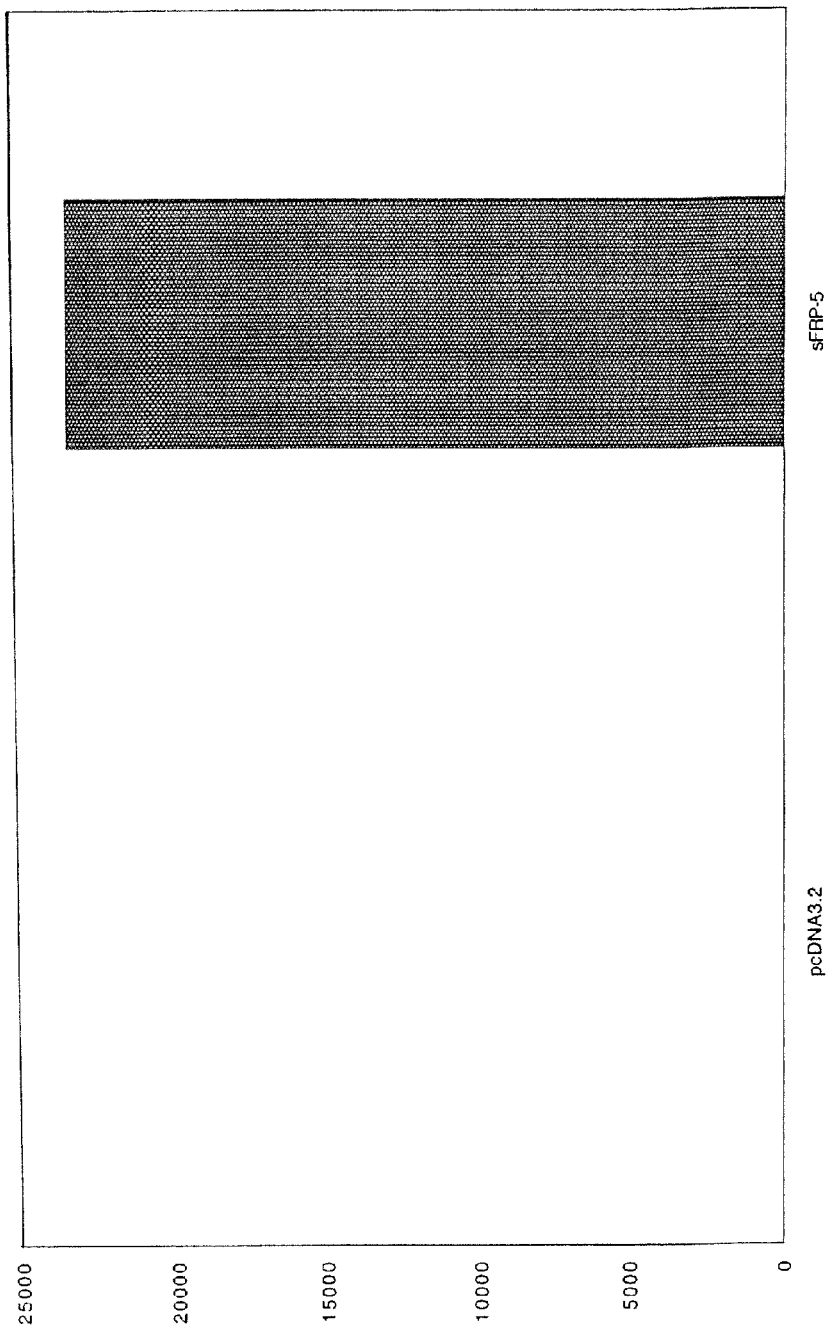
FIG. 5 represents the increased sFRP-5 expression in CHO cells harboring an sFRP-5 expression plasmid.
Figure 6:
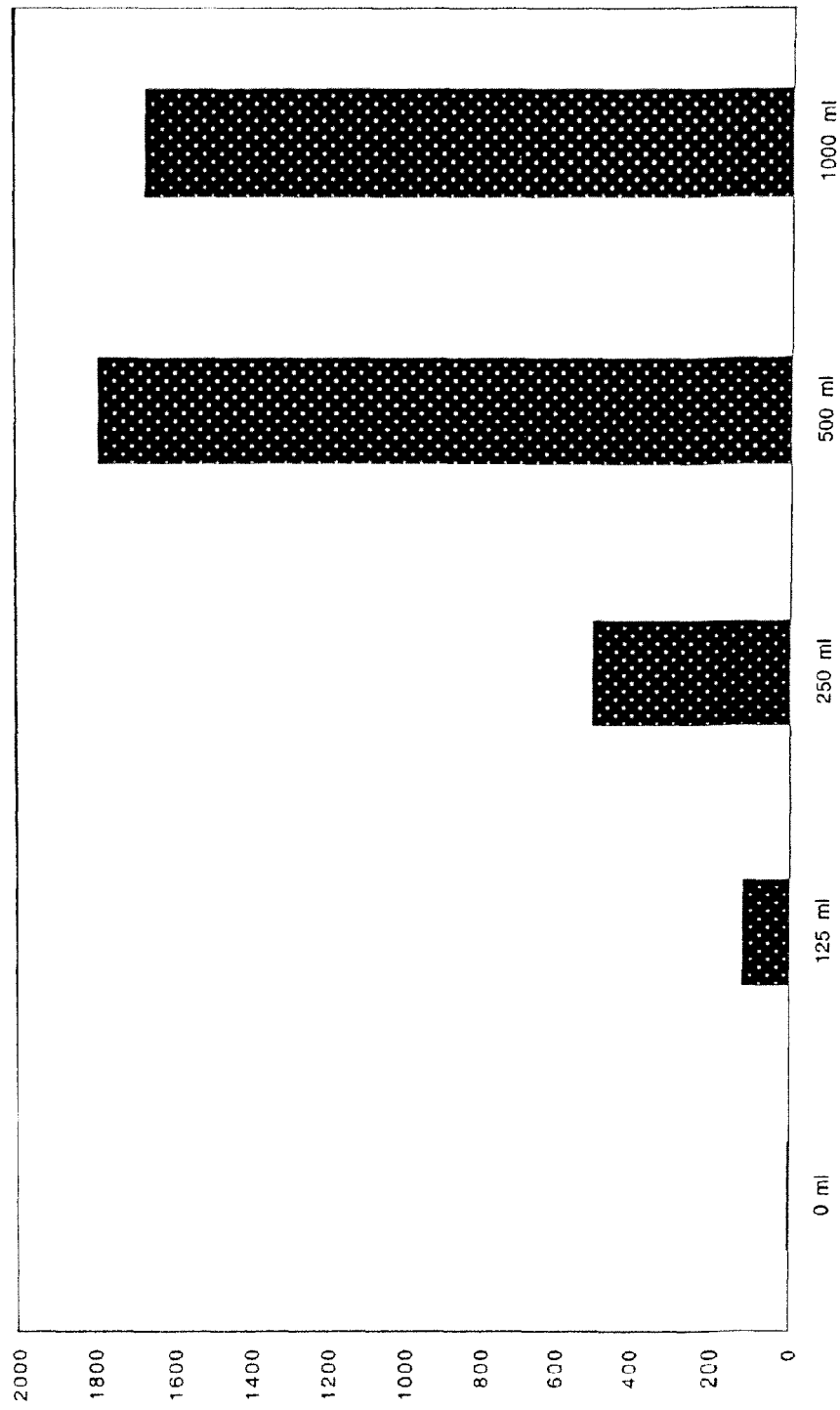
FIG. 6 represents changes sFRP-5 expression levels in response to different doses of conditioned medium containing sFRP-5.

In leptin deficient mice, sFRP-5 expression in the adipose tissue is increased by 6.5-fold (see FIG. 2). The normal expression of sFRP-5 is HMGI-C dependent. Expression of sFRP-5 in white adipose tissue (WAT) is decreased 10-fold in the lean HMGI-C knockout mice as compared to wild-type mice (FIG. 1). sFRP-5 expression in WAT is confined to adipocyte fraction with negligible expression in the stromal vascular fraction (FIG. 3). sFRP-5 also acts in an autocrine fashion to upregulate its own expression in adipocytes. Conditioned medium from CHO cells containing sFRP-5 (FIG. 4) increases endogenous expression of sFRP-5 in 3T3-L1 adipocytes by greater than 1600-fold (FIG. 5). sFRP-5 expression in wild-type mice is most prominent in the adult fat pads. The evidence that sFRP-5 is highly expressed in mature adipocytes as opposed to preadipocytes and the nature of its autocrine upregulation led us to propose that an increase in sFRP-5 activity leads to an increase in the programmed cell death of differentiated adipocytes and thus reduces adiposity. Confirmation of our model came from the transgenic mouse experiments outlined below.

Therapeutic Methods

The SFRP-5 polypeptide or active fragments of the SFRP-5 polypeptides (also referred to herein as "active compounds") of the invention can be incorporated into pharmaceutical compositions suitable for administration. Such compositions typically comprise the polypeptide and a pharmaceutically acceptable carrier. As used herein the language "pharmaceutically acceptable carrier" is intended to include solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Other active compounds can also be incorporated into the compositions.

A pharmaceutical composition of the invention is formulated to be compatible with its intended route of administration. Examples of routes of administration include parenteral, e.g., intravenous, intradermal, subcutaneous, intramuscular, intraperitoneal, nasal, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions, sterile powders and lyophilized preparations, for the preparation of sterile injectable solutions or dispersions. For intravenous administration, suitable carriers include physiological saline, bacteriostatic water, Cremophor EL™ (BASF, Parsippany, N.J.) or phosphate buffered saline (PBS). The composition is sterile and fluid, and stable under the conditions of manufacture and storage. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an sFRP-5 peptide, an active fragment of an SFRP-5 polypeptide or an anti-SFRP-5 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For administration by inhalation, the compounds are delivered in the form of an aerosol spray from pressured container or dispenser which contains a suitable propellant, e.g., a gas such as carbon dioxide, or a nebulizer.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (Palo Alto, Calif.) and Alkermes (Cambridge Mass.). Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

A therapeutically effective amount of polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a polypeptide or antibody can include a single treatment or, preferably, can include a series of treatments.

In an embodiment, a subject is treated with a polypeptide in the range of between about 0.1 to 20 mg/kg body weight, one time per week for between about 1 to 30 weeks, preferably between 4 to 24 weeks, more preferably between about 8 to 20 weeks, and even more preferably for about 12, 15, or 18 weeks. It will also be appreciated that the effective dosage of antibody or polypeptide used for treatment may increase or decrease over the course of a particular treatment. Changes in dosage may result and become apparent from the results of diagnostic assays as described herein.

Experimental Details sFRP-5 Subcloning sFRP-5 cDNA was subcloned as follows. Total RNA from the ob/ob mouse was reverse transcribed using superscript II RT reverse transcriptase. A forward primer SEQ ID NO: 3 (5'-CACCATGTGGGTGGCCTGGAGCGCACGG-3') and reverse primer SEQ ID NO: 4 (5'-CACAGCTGGCTGGT-TGGGGCAA-3') were used to amplify the sFRP-5 coding sequence. The product was purified on a 1% agarose gel and subcloned into the pENTR/D-TOPO plasmid vector. The gene was sequenced and then transferred into the pcDNA3.2/DEST plasmid vector (Invitrogen) via in vitro recombination using the LR clonase enzyme mix (Invitrogen) as recommended by the manufacturer. The pcDNA3.2/sFRP-5 was amplified in *E. coli* and purified using the Midi plasmid isolation kit (Quiagen).

Real Time PCR Analysis of sFRP-5 Expression

Snap-frozen tissues were used to isolate total RNA by the RNeasy protocol (Qiagen Inc. CA). Briefly, tissues were homogenized in the lysis buffer containing guanidine isothiocyanate and applied to the RNeasy column. After several washes to remove contaminants, RNA bound to the column matrix is eluted in distilled water. First strand cDNA is made from 1 µg of total RNA using reverse transcriptase in a standard reaction.

Quantitative real-time PCR using the Applied Biosystems ABI Prism 7900HT sequence detector provides an accurate method for the determination of mRNA levels in a tissue sample. The quantitation is based on the detection of a fluorescent signal produced proportionally during the amplification of a PCR product (see FIG. 4). A probe (TaqMan) is designed to anneal to the sequence of interest between the usual forward and reverse PCR primers. The probe is labelled with a reporter fluorochrome at the 5' end and a quencher either at any T position or at the 3' end. The probe is designed to have a higher Tm than the primers as the probe must be 100% annealed at the extension phase for the assay to be successful. As long as the reporter and the quencher are both attached to the probe, the quencher blocks the fluorescence of the reporter. However, as the Taq polymerase extends the primer, the intrinsic 5'-3' exonuclease activity of the Taq polymerase degrades the probe thereby releasing the reporter. The amount of fluorescence released during the amplification cycle is proportional to the amount of product generated in each cycle.

Cell Culture

Briefly, transient expression of sFRP-5 in Chinese hamster ovary (CHO) cells was carried out as follows. CHO cells were seeded in a dish of 6 cm diameter and cultured in Ham's F12K medium adjusted to 2 mM L-glutamine and to 1.5 g/L of sodium bicarbonate and containing 10% fetal bovine serum. The cells were maintained at 37° C. in a humidified atmosphere of 5% $CO_2$. Cultures were grown to 90% confluence and were transfected with 8 µg pcDNA3.2/DEST-sfrp5 DNA or pcDNA3.2DEST as a negative control with Lipofectamine 2000 (Invitrogen) as recommended by the manufacturer. After 6 hours of incubation, the cells were washed with PBS and growth medium was added for incubation for 48 hours, at which point the conditioned medium containing secreted sFRP-5 was collected for further study.

Assays for sFRP-5 mRNA Expression Levels

3T3-L1 cells were grown in 6 cm diameter plates in Dulbecco's Modified Eagle Medium (DMEM) adjusted to 4 mM L-glutamine, to 1.5 g/L of Sodium Bicarbonate, and to 4.5 g/L glucose and containing 10% fetal bovine serum. The cells were maintained at 37° C. in a humidified atmosphere of 5% CO2. At full confluence the cells were supplemented with conditioned medium containing sFRP-5 in amounts described in FIG. 4. Maximal autocrine stimulation of sFRP-5 expression in 3T3-L1 cells was achieved at a dose of 500 µl conditioned medium per 5 ml of growth medium. After 6 days of incubation, the cells were collected and total RNA was isolated using the Rneasy kit (Quiagen). Random primer cDNA was synthesized using Superscript II (Invitrogen). Real time quantitative PCR (TaqMan) for sFRP-5 and the GAPDH control was performed in the Applied biosystems ABI 7900HT Thermocycler using the recommended reagents and protocols of the manufacturer. The primers and TaqMan sequences are as follows:

sFRP-5:
SEQ ID NO: 5    (forward)  5'-TGTGCCCAGTGTGAGATGGA-3'

SEQ ID NO: 6    (reverse)  5'-GCGCATCTTGACCACAAAGTC-3'

SEQ ID NO: 7    (probe)    6FAM-TGACGGCCTCATGGAACAGATGT
                           GC-TAMRA GAPDH Control:
SEQ ID NO: 8    (forward)  5'-CAACGGGAAGCCCATCAC-3'

SEQ ID NO: 9    (reverse)  5'-CGGCCTCACCCCATTTG-3'

SEQ ID NO: 10   (probe)    VIC-ATCTTCCAGGAGCGAGACCCC
                           ACTAACA-TAMRA Similar experiments were conducted using conditioned medium from pcDNA3.2/DEST-sfrp5 transfected 3T3-L1 cells with substantially identical results.

sFRP-5 Transgenic Mice

Figure 7:
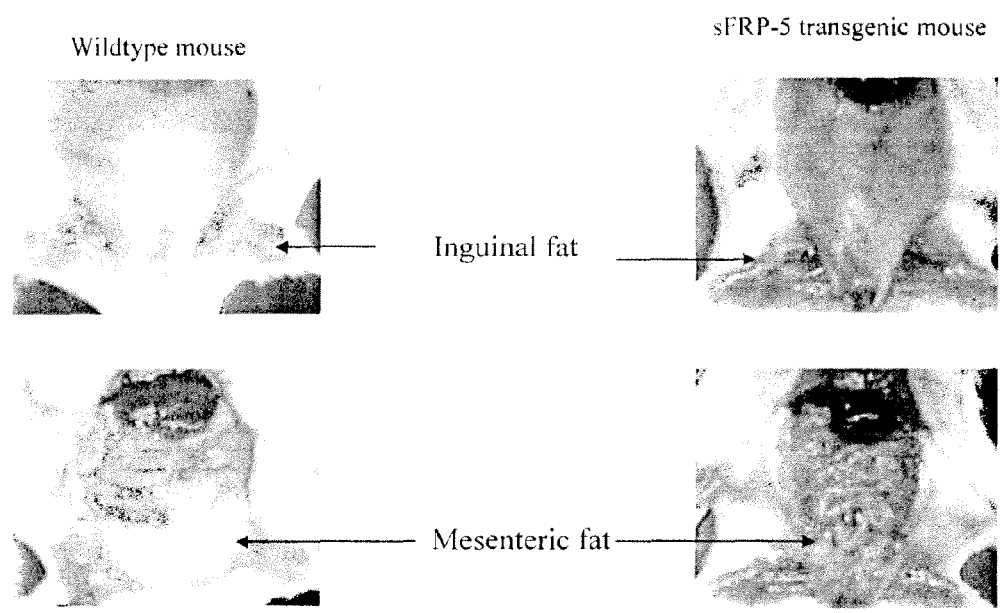
FIG. 7 represents the effects of overexpression of sFRP-5 on adipose tissue in transgenic mice overexpressing sFRP-5 under the control of the adipose specific aP2 promoter.

In order to confirm that administration of sFRP-5 would result in a reduction of adiposity we produced three independent lines of sFRP-5 transgenic mice overexpressing the sFRP-5 polypeptide under the control of the adipocyte specific aP2 promoter. (Murine sFRP-5 sequence may be found under Genbank accession number NM_018780.) Of these lines, 2 out of three showed a significant reduction in weight by 18 weeks of age. Dissection of mice of the highest expressing line revealed a greater than 90% decrease in mass of the inguinal and mesenteric fat pads (see FIG. 7). These results demonstrate that an increase in sFRP-5 polypeptide results in a significant decrease in adipocytes, most likely through promoting an increase in programmed cell death of differentiated, mature adipocytes. Thus, administration of sFRP-5 at a therapeutic dosage will result in a decrease in adipocyte mass in a subject and thus will be beneficial in the treatment of obesity and obesity related complications.

What is claimed is:

1. A method of promoting apoptosis of differentiated adipocytes in a subject in need thereof comprising administering to the subject an amount of a recombinant sFRP-5 peptide effective to promote apoptosis of the differentiated adipocytes.

2. The method of claim 1, wherein the subject is human.

3. The method of claim 1, wherein the administration is parenteral, intradermal, transdermal, transmucosal, rectal, subcutaneous, or by inhalation.

4. A method of increasing endogenous expression of sFRP-5 peptide by adipocytes in a subject in need thereof comprising administering to the subject an amount of a recombinant sFRP-5 peptide effective to increase endogenous expression of sFRP-5 peptide by adipocytes.

5. The method of claim 4, wherein the subject is human.

6. The method of claim 4, wherein the administration is parenteral, intradermal, transdermal, transmucosal, rectal, subcutaneous, or by inhalation.

* * * * *

UNITED STATES PATENT AND TRADEMARK OFFICE
CERTIFICATE OF CORRECTION

PATENT NO. : 8,211,853 B2
APPLICATION NO. : 12/803963
DATED : July 3, 2012
INVENTOR(S) : Kiran K. Chada et al.

Page 1 of 1

It is certified that error appears in the above-identified patent and that said Letters Patent is hereby corrected as shown below:

On the title page, INID code (63) should read as follows:

"Continuation of application U.S. Serial No. 10/768,566, filed Jan. 29, 2004, now abandoned, which was a continuation of U.S. Serial No. 10/630,423, filed Jul. 29, 2003, now U.S. Patent No. 7,879,544, issued Feb. 1, 2011."

On the title page, INID code (60) should read as follows:

"Provisional application No. 60/398,785, filed on Jul. 29, 2002, provisional application No. 60/478,206, filed on Jun. 12, 2003."

Col. 1, lines 7-12 of the specification should read as follows:

"This application is a continuation of U.S. Serial No. 10/768,566, filed January 29, 2004, which claims benefit of U.S. Serial No. 10/630,423, filed July 29, 2003, which claims benefit of U.S. Provisional Application No. 60/398,785, filed July 29, 2002, and U.S. Provisional Application No. 60/478,206, filed June 12, 2003, the contents of all of which are hereby incorporated by reference."

Signed and Sealed this
Twenty-third Day of October, 2012

David J. Kappos
*Director of the United States Patent and Trademark Office*

SEQUENCE LISTING

<160> NUMBER OF SEQ ID NOS: 10

<210> SEQ ID NO 1
<211> LENGTH: 317
<212> TYPE: PRT
<213> ORGANISM: Human

<400> SEQUENCE: 1

Met Arg Ala Ala Ala Ala Gly Gly Val Arg Thr Ala Ala Leu Ala
1               5                   10                  15

Leu Leu Leu Gly Ala Leu His Trp Ala Pro Ala Arg Cys Glu Glu Tyr
                20                  25                  30

Asp Tyr Tyr Gly Trp Gln Ala Glu Pro Leu His Gly Arg Ser Tyr Ser
            35                  40                  45

Lys Pro Pro Gln Cys Leu Asp Ile Pro Ala Asp Leu Pro Leu Cys His
50                  55                  60

Thr Val Gly Tyr Lys Arg Met Arg Leu Pro Asn Leu Leu Glu His Glu
65                  70                  75                  80

Ser Leu Ala Glu Val Lys Gln Gln Ala Ser Ser Trp Leu Pro Leu Leu
                85                  90                  95

Ala Lys Arg Cys His Ser Asp Thr Gln Val Phe Leu Cys Ser Leu Phe
                100                 105                 110

Ala Pro Val Cys Leu Asp Arg Pro Ile Tyr Pro Cys Arg Ser Leu Cys
                115                 120                 125

Glu Ala Val Arg Ala Gly Cys Ala Pro Leu Met Glu Ala Tyr Gly Phe
                130                 135                 140

Pro Trp Pro Glu Met Leu His Cys His Lys Phe Pro Leu Asp Asn Asp
145                 150                 155                 160

Leu Cys Ile Ala Val Gln Phe Gly His Leu Pro Ala Thr Ala Pro Pro
                165                 170                 175

Val Thr Lys Ile Cys Ala Gln Cys Glu Met Glu His Ser Ala Asp Gly
                180                 185                 190

Leu Met Glu Gln Met Cys Ser Ser Asp Phe Val Val Lys Met Arg Ile
                195                 200                 205

Lys Glu Ile Lys Ile Glu Asn Gly Asp Arg Lys Leu Ile Gly Ala Gln
                210                 215                 220

Lys Lys Lys Lys Leu Leu Lys Pro Gly Pro Leu Lys Arg Lys Asp Thr
225                 230                 235                 240

Lys Arg Leu Val Leu His Met Lys Asn Gly Ala Gly Cys Pro Cys Pro
                245                 250                 255

Gln Leu Asp Ser Leu Ala Gly Ser Phe Leu Val Met Gly Arg Lys Val
                260                 265                 270

Asp Gly Gln Leu Leu Leu Met Ala Val Tyr Arg Trp Asp Lys Lys Asn
                275                 280                 285

Lys Glu Met Lys Phe Ala Val Lys Phe Met Phe Ser Tyr Pro Cys Ser
                290                 295                 300

Leu Tyr Tyr Pro Phe Phe Tyr Gly Ala Ala Glu Pro His
305                 310                 315

<210> SEQ ID NO 2
<211> LENGTH: 1905
<212> TYPE: DNA
<213> ORGANISM: Human

<400> SEQUENCE: 2

-continued

```
gaggcgccag gatcagtcgg ggcacccgca gcgcaggctg ccacccacct gggcgacctc      60
cgcggcggcg gcggcggcgg ctgggtagag tcagggccgg gggcgcacgc cggaacacct     120
gggccgccgg gcaccgagcg tcgggggget gcgcggcgcg accctggaga gggcgcagcc     180
gatgcgggcg gcggcggcgg cgggggggcgt gcggacggcc gcgctggcgc tgctgctggg     240
ggcgctgcac tgggcgccgg cgcgctgcga ggagtacgac tactatggct ggcaggccga     300
gccgctgcac ggccgctcct actccaagcc gccgcagtgc cttgacatcc ctgccgacct     360
gccgctctgc cacacggtgg gctacaagcg catgcggctg cccaacctgc tggagcacga     420
gagcctggcc gaagtgaagc agcaggcgag cagctggctg ccgctgctgg ccaagcgctg     480
ccactcggat acgcaggtct tcctgtgctc gctctttgcg cccgtctgtc tcgaccggcc     540
catctacccg tgccgctcgc tgtgcgaggc cgtgcgcgcc ggctgcgcgc cgctcatgga     600
ggcctacggc ttcccctggc ctgagatgct gcactgccac aagttccccc tggacaacga     660
cctctgcatc gccgtgcagt tcgggcacct gcccgccacc gcgcctccag tgaccaagat     720
ctgcgcccag tgtgagatgg agcacagtgc tgacggcctc atggagcaga tgtgctccag     780
tgactttgtg gtcaaaatgc gcatcaagga gatcaagata gagaatgggg accgaaagct     840
gattggagcc cagaaaaaga agaagctgct caagccgggc cccctgaagc gcaaggacac     900
caagcggctg gtgctgcaca tgaagaatgg cgcgggctgc ccctgcccac agctggacag     960
cctggcgggc agcttcctgg tcatgggccg caaagtggat ggacagctgc tgctcatggc    1020
cgtctaccgc tgggacaaga agaataagga gatgaagttt gcagtcaaat tcatgttctc    1080 ctaccctgc tccctctact acccttctt ctacggggcg gcagagcccc actgaagggc     1140
actcctcctt gccctgccag ctgtgccttg cttgccctct ggccccgccc caacttccag    1200
gctgacccgg ccctactgga gggtgttttc acgaatgttg ttactggcac aaggcctaag    1260
ggatgggcac ggagcccagg ctgtccttt tgacccaggg gtcctgggt ccctgggatg     1320 ttgggcttcc tctctcagga gcagggcttc ttcatctggg tgaagacctc agggtctcag    1380
aaagtaggca ggggaggaga gggtaaggga aaggtggagg ggctcagggc accctgaggc    1440
ggaggtttca gagtagaagg tgatgtcagc tccagctccc ctctgtcggt ggtggggcct    1500
caccttgaag agggaagtct caatattagg ctaagctatt tgggaaagtt ctccccaccg    1560
cccctgtacg cgtcatccta gccccccttg ggaaaggagt tagggtctca gtgcctccag    1620 ccacacccc tgccttcccc agcttgccca tttccctgcc ccaaggccca gagctccccc    1680
cagactggag agcaagccca gcccagcctc ggcatagacc cccttctggt ccgcccgtgg    1740
ctcgattccc gggattcatt cctcagcctc tgcttctccc ttttatccca ataagttatt    1800
gctactgctg tgaggccata ggtactagac aaccaataca tgcagggttg ggttttctaa    1860
tttttttaac ttttaattaa aatcaaaggt cgacgcgcgg ccgcg               1905
```

```
<210> SEQ ID NO 3
<211> LENGTH: 28
<212> TYPE: DNA
<213> ORGANISM: Mouse

<400> SEQUENCE: 3
caccatgtgg gtggcctgga gcgcacgg                                          28

<210> SEQ ID NO 4
<211> LENGTH: 22
<212> TYPE: DNA
<213> ORGANISM: Mouse
```

```
-continued

<400> SEQUENCE: 4
cacagctggc tggttggggc aa                                            22

<210> SEQ ID NO 5
<211> LENGTH: 20
<212> TYPE: DNA
<213> ORGANISM: Mouse

<400> SEQUENCE: 5
tgtgcccagt gtgagatgga                                               20

<210> SEQ ID NO 6
<211> LENGTH: 21
<212> TYPE: DNA
<213> ORGANISM: Mouse

<400> SEQUENCE: 6
gcgcatcttg accacaaagt c                                             21

<210> SEQ ID NO 7
<211> LENGTH: 25
<212> TYPE: DNA
<213> ORGANISM: Mouse

<400> SEQUENCE: 7
tgacggcctc atggaacaga tgtgc                                         25

<210> SEQ ID NO 8
<211> LENGTH: 18
<212> TYPE: DNA
<213> ORGANISM: Mouse

<400> SEQUENCE: 8
caacgggaag cccatcac                                                 18

<210> SEQ ID NO 9
<211> LENGTH: 17
<212> TYPE: DNA
<213> ORGANISM: Mouse

<400> SEQUENCE: 9
cggcctcacc ccatttg                                                  17

<210> SEQ ID NO 10
<211> LENGTH: 28
<212> TYPE: DNA
<213> ORGANISM: Mouse

<400> SEQUENCE: 10
atcttccagg agcgagaccc cactaaca                                      28
```